US012682994B2

(12) United States Patent
Matsuura

(10) Patent No.: US 12,682,994 B2
(45) Date of Patent: Jul. 14, 2026

(54) INFORMATION PROCESSING APPARATUS, INFORMATION PROCESSING METHOD, AND INFORMATION PROCESSING PROGRAM

(71) Applicant: FUJIFILM Corporation, Tokyo (JP)

(72) Inventor: Takayuki Matsuura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/624,104

(22) Filed: Apr. 1, 2024

(65) Prior Publication Data

US 2024/0242800 A1 Jul. 18, 2024

Related U.S. Application Data

(63) Continuation of application No. PCT/JP2022/036997, filed on Oct. 3, 2022.

(30) Foreign Application Priority Data

Oct. 15, 2021 (JP) ................................. 2021-169822

(51) Int. Cl.
*G16H 10/60* (2018.01)
(52) U.S. Cl.
CPC .................................... *G16H 10/60* (2018.01)
(58) Field of Classification Search
None
See application file for complete search history.

(56) References Cited

U.S. PATENT DOCUMENTS

| | | | |
|---|---|---|---|
| 2008/0275731 A1* | 11/2008 | Rao | G16H 10/60 705/3 |
| 2016/0019347 A1* | 1/2016 | Boston | G16Z 99/00 705/3 |
| 2020/0342997 A1* | 10/2020 | Mitsumori | G16H 50/20 |

(Continued)

FOREIGN PATENT DOCUMENTS

| | | |
|---|---|---|
| JP | 2006155002 | 6/2006 |
| JP | 2018013825 | 1/2018 |

(Continued)

OTHER PUBLICATIONS

"International Search Report (Form PCT/ISA/210) of PCT/JP2022/036997," mailed on Nov. 15, 2022, with English translation thereof, pp. 1-5.

(Continued)

*Primary Examiner* — Katherine Kolosowski-Gager
(74) *Attorney, Agent, or Firm* — JCIPRNET

(57) ABSTRACT

An information processing apparatus includes at least one processor. The processor is configured to: acquire designation information for designating a plurality of derivation methods to derive record information to be recorded in at least one record item related to a patient; derive the record information by applying a derivation method, which is selected according to a preset priority order from among the plurality of derivation methods designated through the designation information, based on patient information related to the patient, for the record item; and generate medical document data in which the derived record information is recorded in the record item.

8 Claims, 13 Drawing Sheets

(56) References Cited

U.S. PATENT DOCUMENTS

2023/0082381 A1 * 3/2023 Gnanasambandam .. G06N 5/02
705/4

FOREIGN PATENT DOCUMENTS

| JP | 2020135056 | 8/2020 |
| JP | 2020181342 | 11/2020 |

OTHER PUBLICATIONS

"Written Opinion of the International Searching Authority (Form PCT/ISA/237) of PCT/JP2022/036997," mailed on Nov. 15, 2022, with English translation thereof, pp. 1-8.

"Office Action of Japan Counterpart Application", issued on Sep. 9, 2025, with English translation thereof, pp. 1-6.

"Decision of Refusal of Japan Counterpart Application", issued on Dec. 9, 2025, with English translation thereof, p. 1-p. 5.

* cited by examiner

PATIENT
INFORMATION

INFORMATION
PROCESSING
APPARATUS

RECORD
INFORMATION

NAME: _____
DATA OF BIRTH:_____     AGE: _____
HEIGHT:_____ cm     WEIGHT:_____ kg

Q1     • • • • • • • • •
ANSWER:_____

Q2     • • • • • • • • •
ANSWER:_____

Q3     • • • • • • • • •
ANSWER:_____

101 CPU

102 RAM

106 NETWORK I/F

107

NON-VOLATILE MEMORY

DOCUMENT CREATION PROGRAM — 110

DETERMINATION /CLASSIFICATION RULE — 111

DETERMINATION /CLASSIFICATION MODEL — 112

DESIGNATION INFORMATION — 113

EXCHANGE DATA — 114

103

DISPLAY

105

INPUT DEVICE

104

113

| DETERMINATION ITEM | FIRST PRIORITY ORDER | SECOND PRIORITY ORDER |
|---|---|---|
| ITEM 1 | FIRST DERIVATION METHOD | SECOND DERIVATION METHOD |
| ITEM 2 | THIRD DERIVATION METHOD | SECOND DERIVATION METHOD |
| ITEM 3 | FIRST DERIVATION METHOD | FIRST DERIVATION METHOD |
| ITEM 4 | THIRD DERIVATION METHOD | THIRD DERIVATION METHOD |

FIG. 6

Q2 HAVE YOU LOST YOUR APPETITE AND EATEN LESS IN LAST 1 TO 2 MONTHS?

☐ NO ☑ YES

Q3 PLEASE PUT O IN FIELD THAT APPLIES TO YOUR DAILY LIFE.

|  | I CAN DO IT BY MYSELF | NEED NURSING CARE /ASSISTANCE |
|---|---|---|
| EATING | ☐ | ☑ |
| WASHING | ☑ | ☐ |
| BATHING | ☐ | ☑ |
| WALKING | ☐ | ☑ |
| CHANGING CLOTHES | ☐ | ☑ |
| EXCRETING | ☑ | ☐ |

~21

⇩

DETERMINATION /CLASSIFICATION MODEL ~112

⇩

| DETERMINATION ITEM | DETERMINATION RESULTS |
|---|---|
| ITEM 2 (ADL) | ☑ NEED NURSING CARE/ASSISTANCE |

Figure 7:
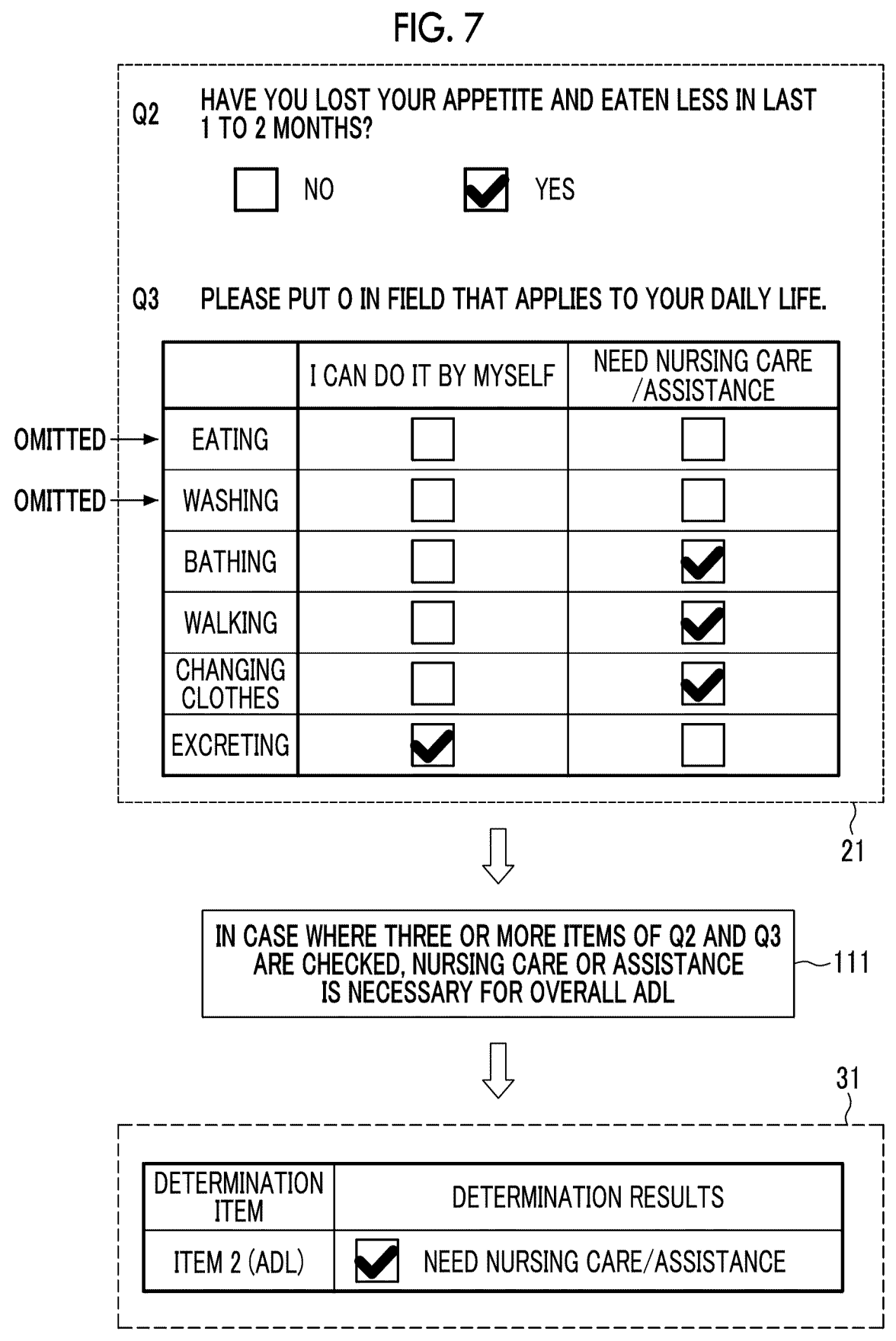

Q2   HAVE YOU LOST YOUR APPETITE AND EATEN LESS IN LAST 1 TO 2 MONTHS?

☐ NO          ✓ YES

Q3   PLEASE PUT O IN FIELD THAT APPLIES TO YOUR DAILY LIFE.

| | I CAN DO IT BY MYSELF | NEED NURSING CARE /ASSISTANCE |
|---|---|---|
| EATING | ☐ | ☐ |
| WASHING | ☐ | ☐ |
| BATHING | ☐ | ✓ |
| WALKING | ☐ | ✓ |
| CHANGING CLOTHES | ☐ | ✓ |
| EXCRETING | ✓ | ☐ |

OMITTED → EATING
OMITTED → WASHING

21

IN CASE WHERE THREE OR MORE ITEMS OF Q2 AND Q3 ARE CHECKED, NURSING CARE OR ASSISTANCE IS NECESSARY FOR OVERALL ADL    ~111

31

| DETERMINATION ITEM | DETERMINATION RESULTS |
|---|---|
| ITEM 2 (ADL) | ✓ NEED NURSING CARE/ASSISTANCE |

| ITEM NAME OF PATIENT INFORMATION | | ITEM NAME OF RECORD INFORMATION | |
|---|---|---|---|
| TIME-OF-TRAINING ITEM NAME | ACTUALLY-USED ITEM NAME | TIME-OF-TRAINING ITEM NAME | ACTUALLY-USED ITEM NAME |
| a | D | | |
| b | E | X | Y |
| c | F | | |

INFORMATION PROCESSING APPARATUS, INFORMATION PROCESSING METHOD, AND INFORMATION PROCESSING PROGRAM

This application is a continuation application of International Application No. PCT/JP2022/036997, filed Oct. 3, 2022, the disclosure of which is incorporated herein by reference in its entirety. Further, this application claims priority from Japanese Patent Application No. 2021-169822 filed on Oct. 15, 2021, the disclosures of which is incorporated herein by reference in its entirety.

BACKGROUND

1. Technical Field

The disclosed technology relates to an information processing apparatus, an information processing method, and an information processing program.

2. Description of the Related Art

The following technology is known as a technology for processing information related to a specific patient. For example, JP2018-13825A discloses an introduction letter creation support system including: a first database that stores medical information for each patient; a second database that stores information for creating an introduction letter; a medical information acquisition unit that acquires the medical information related to a predetermined patient from the first database; an inference unit that performs inference based on the medical information acquired by the medical information acquisition unit and the information stored in the second database; and a creation processing unit that creates at least a part of the introduction letter for the corresponding patient by inputting the information, which is acquired by the inference unit, into a predetermined template.

JP2020-135056A discloses a medical information processing system including: an acquisition unit that acquires reference information related to medical treatment information included in a medical treatment information provision document; a determination unit that determines whether or not the medical treatment information included in the medical treatment information provision document is sufficient information for a medical institution, which is a provision destination, based on the reference information; and a control unit that controls such that information, which is based on a determination result obtained by the determination unit, is presented to the medical institution, which is a provision source.

SUMMARY

One embodiment according to the present disclosed technology provides an information processing apparatus, an information processing method, and an information processing program capable of effectively supporting the creation of medical documents, as compared with a case where a plurality of derivation methods are not designated for deriving record information to be recorded in at least one record item related to a patient.

An information processing apparatus according to the disclosed technology comprises: at least one processor, in which the processor is configured to: acquire designation information for designating a plurality of derivation methods to derive record information to be recorded in at least one record item related to a patient; derive the record information by applying a derivation method, which is selected according to a preset priority order from among the plurality of derivation methods designated through the designation information, based on patient information related to the patient, for the record item; and generate medical document data in which the derived record information is recorded in the record item.

The processor may in a case where the record information is not capable of being derived by using a derivation method where a relatively high priority order is set among the plurality of derivation methods, derive the record information by using a derivation method where a relatively low priority order is set.

At least one of the plurality of derivation methods may be a first derivation method of deriving the record information by diversion from the patient information, a second derivation method of deriving the record information by performing determination or classification based on a predetermined rule regarding the patient information, or a third derivation method of deriving the record information by performing determination or classification using a trained model regarding the patient information. The trained model may be a model that uses the patient information as an input and that uses the record information as an output.

The processor may in a case where the third derivation method is applied, regarding the patient information, use exchange data, which indicates a correspondence relationship between an item name actually used and an item name used at a time of training of the trained model, to specify the patient information of the item name actually used corresponding to the item name used at the time of training, and derive the record information by inputting the specified patient information to the trained model.

The processor may present the medical document data by associating information, which indicates the derivation method applied to derive the record information from among the plurality of derivation methods, with the record information. The processor may present the medical document data by associating the patient information, which is used to derive the record information, with the record information. The processor may receive a designation input of the designation information.

The medical document data may be data obtained by converting documents, which are related to hospital admission and discharge of the patient, into data.

An information processing method according to the disclosed technology is a method executed by at least one processor included in an information processing apparatus, the method comprises: acquiring designation information for designating a plurality of derivation methods to derive record information to be recorded in at least one record item related to a patient; deriving the record information by applying a derivation method, which is selected according to a preset priority order from among the plurality of derivation methods designated through the designation information, based on patient information related to the patient, for the record item; and generating medical document data in which the derived record information is recorded in the record item.

An information processing program according to the disclosed technology is a program causing at least one processor included in an information processing apparatus to execute a process comprising: acquiring designation information for designating a plurality of derivation methods to derive record information to be recorded in at least one record item related to a patient; deriving the record information by applying a derivation method, which is selected according to a preset priority order from among the plurality of derivation methods designated through the designation information, based on patient information related to the patient, for the record item; and generating medical document data in which the derived record information is recorded in the record item.

BRIEF DESCRIPTION OF THE DRAWINGS

Exemplary embodiments according to the technique of the present disclosure will be described in detail based on the following figures, wherein:

FIG. 2A is a diagram showing an example of a schematic content of first medical document data according to the embodiment of the disclosed technology;

FIG. 2B is a diagram showing an example of a schematic content of second medical document data according to the embodiment of the disclosed technology;

FIG. 6 is a diagram showing an example of an aspect in which a derivation unit according to the embodiment of the disclosed technology derives record information by using a third derivation method;

FIG. 7 is a diagram showing an example of an aspect in which the derivation unit according to the embodiment of the disclosed technology derives the record information by using the third derivation method;

DETAILED DESCRIPTION

Figure 1:
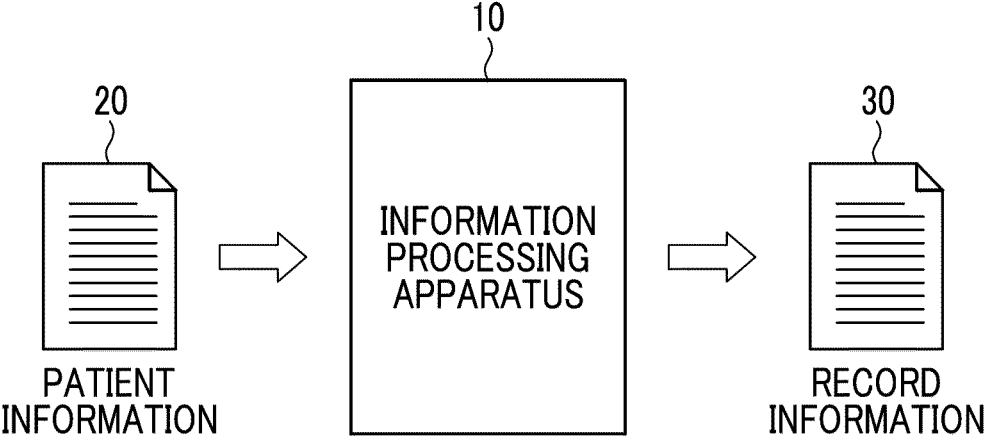
FIG. 1 is a diagram showing a function of an information processing apparatus according to an embodiment of the disclosed technology.

Hereinafter, an example of an embodiment of the disclosed technology will be described with reference to the drawings. The same or equivalent components and portions in the drawings are assigned by the same reference numerals, and the overlapping description will be omitted.

As shown in FIG. 1, first medical document data 20 including patient information related to a patient is input to an information processing apparatus 10 according to an embodiment of the disclosed technology. The information processing apparatus 10 derives record information related to the patient based on the patient information included in the first medical document data 20 and generates second medical document data 30 in which the derived record information is recorded.

Figure 2A:
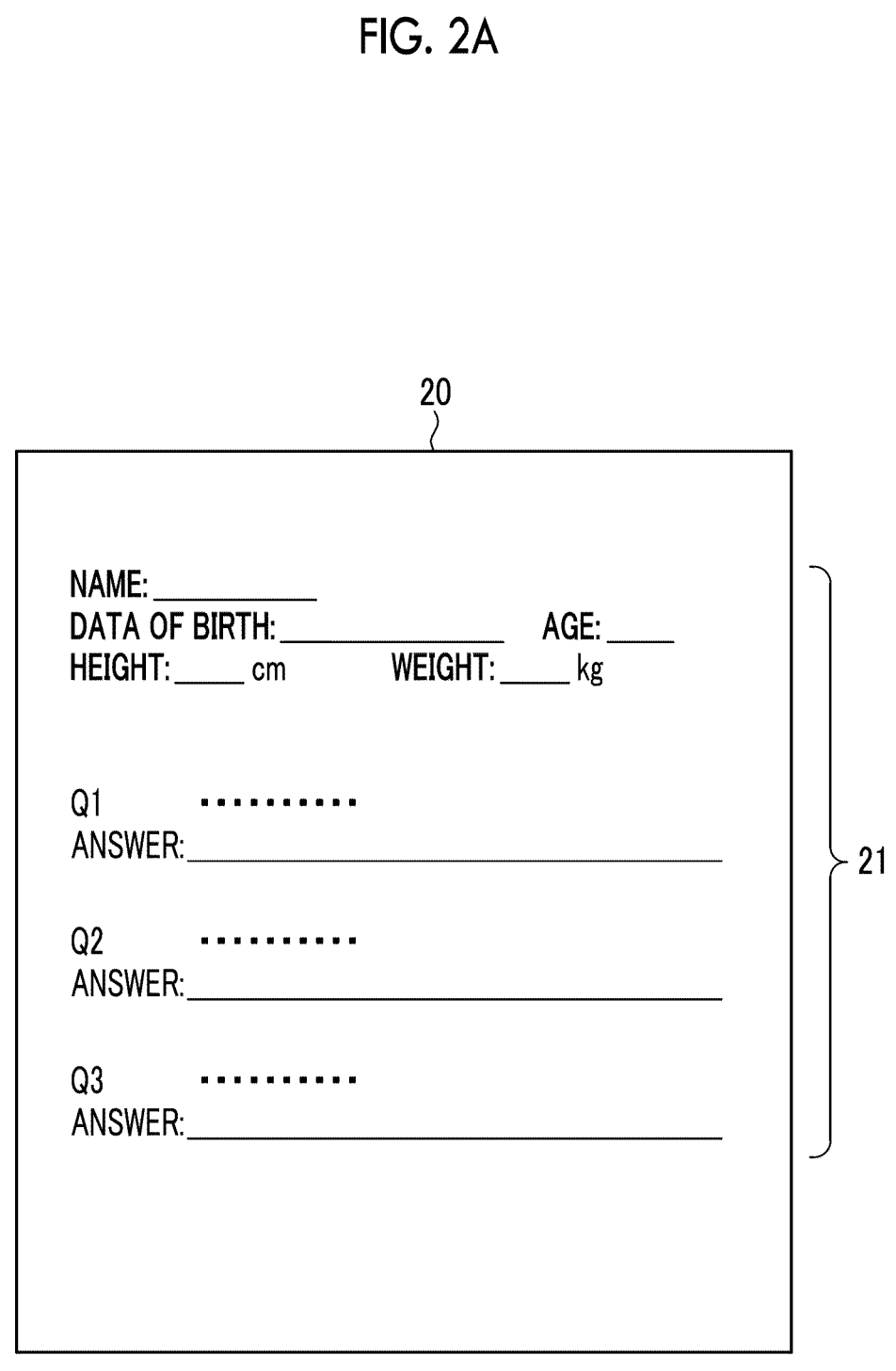

FIG. 2A is a diagram showing an example of a schematic content of the first medical document data 20. The first medical document data 20 may include basic information related to the patient such as a name, a date of birth, an age, a height, and a weight of the patient, as the patient information 21. Further, the first medical document data 20 may include, as the patient information 21, information related to physical and mental of the patient (disease/medical history, medication status, presence or absence of dementia, presence or absence of behavior such as wandering or the like), information related to the living environment (family composition, living history, caregiver's care method, family caregiver's status, or the like), and information related to activities of daily living that can be carried out by the patient and activities of living that require nursing care or assistance. The patient information 21 may be recorded for each item, for example, as an answer to a plurality of questions expressed as Q1, Q2, in FIG. 2A. That is, the patient information 21 may be information to be recorded in a plurality of items included in the first medical document data 20. Further, the patient information 21 may be recorded by checking a check box corresponding to each item. Further, the patient information 21 may be recorded by describing a text for each item. Further, for example, various measurement values, which are obtained through a blood test, a urine test, or the like, may be recorded as the patient information 21.

Although the first medical document data 20 is not particularly limited, for example, the first medical document data 20 may be data obtained by converting medical documents, which are related to hospital admission and discharge of the patient, into data or may be data obtained by converting information sheet at the time of hospital admission (or information coordination sheet at the time of hospital admission) or a medical document, which is created for a similar purpose of the information sheet at the time of hospital admission, into data. For example, the information related to physical and mental of the patient (disease/medical history, medication status, presence or absence of dementia, presence or absence of behavior such as wandering or the like), the information related to the living environment (family composition, living history, caregiver's care method, family caregiver's status, or the like), and information related to activities of daily living that can be carried out by the patient and activities of living that require assistance, are entered in the information sheet at the time of hospital admission. The purpose of the information sheet at the time of hospital admission, in a case where a person living at home is hospitalized, is to confirm the coordination between the home care team and the medical institution, to smoothly promote in-hospital care and hospital discharge support/home care transition support, and to help the patient continue living in the community and improve patient's quality of life (QOL) by local comprehensive support centers or home care support offices, which are already involved in home care, informing the medical institution of the patient's physical and mental condition, living environment, or the like. The information sheet at the time of hospital admission is created by a care manager or the like who holds an interview with the patient, the patient's family, or these people immediately before a timing of the hospital admission. The first medical document data 20 may be generated by converting the medical document as exemplified above into data by using a known character recognition technology such as optical character recognition (OCR). Further, the first medical document data 20 may be data obtained by converting contents described in a plurality of medical documents into data.

Figure 2B:
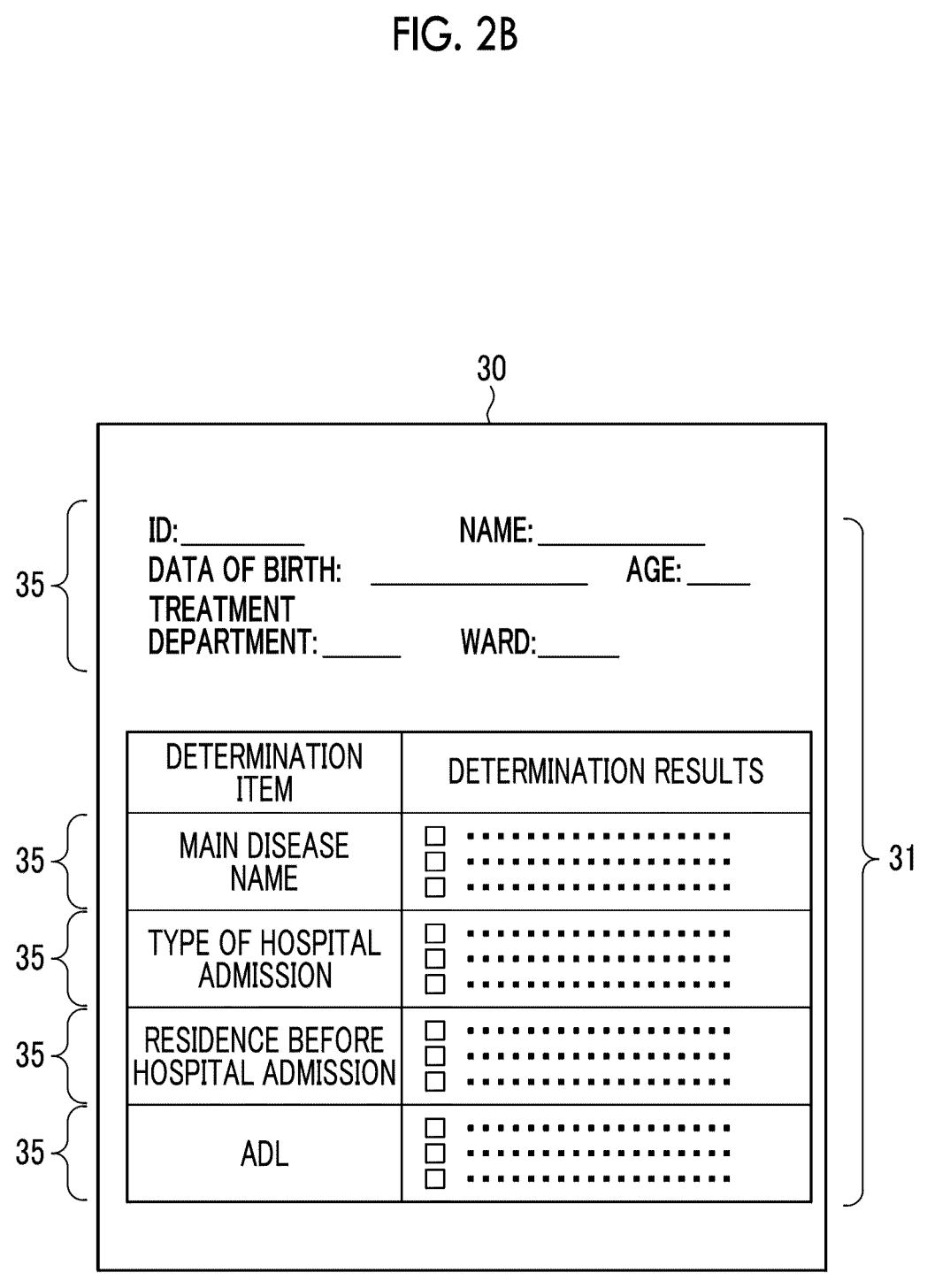

FIG. 2B is a diagram showing an example of a schematic content of the second medical document data 30. The second medical document data 30 includes a plurality of record items 35 in which the record information 31 as exemplified below is recorded. The second medical document data 30 may include, for example, basic information related to the patient such as an identification (ID) for identifying the patient, a name, a date of birth, and an age of the patient, as the record information 31. Further, the second medical document data 30 may include, for example, hospital information related to a treatment department or a ward in which the patient is hospitalized, as the record information 31. Further, the second medical document data 30 may include, for example, medical information related to a main disease name at the time of hospital admission, type of hospital admission (emergency hospital admission, re-hospital admission, repeated hospital admissions and discharges), residence before hospital admission (hospital, facility), and a necessity of nursing care or assistance in activities of daily living (ADL), as the record information 31. The record information 31 may be recorded by checking a check box corresponding to each item. Further, the record information 31 may be recorded by describing a text for each item.

Although the second medical document data 30 is not particularly limited, the second medical document data 30 may be data obtained by converting the medical documents, which are related to hospital admission and discharge of the patient, into data or may be data obtained by converting a hospital discharge support risk screening sheet or a medical document, which is created for a similar purpose of the hospital discharge support risk screening sheet, into data. In this case, the record information 31 may include information related to a necessity of nursing care or assistance for the patient. For example, the information related to the main disease name at the time of hospital admission, the type of hospital admission (emergency hospital admission, re-hospital admission, repeated hospital admissions and discharges), the residence before the hospital admission (hospital, facility), and a necessity of nursing care or assistance in activities of daily living (ADL) are entered in the hospital discharge support risk screening sheet. The purpose of the hospital discharge support risk screening sheet is to evaluate whether or not hospital discharge support/hospital discharge adjustment is needed for the patient/family immediately after the patient is hospitalized and to clarify the support needed for transitioning from a place of treatment to a place of living. The hospital discharge support risk screening sheet is created by a medical worker at a patient hospital at a relatively early time (for example, within 3 days after the hospital admission) after the hospital admission of the patient. The second medical document data 30 is created at a time point later than a creation time point of the first medical document data 20.

Figure 3:
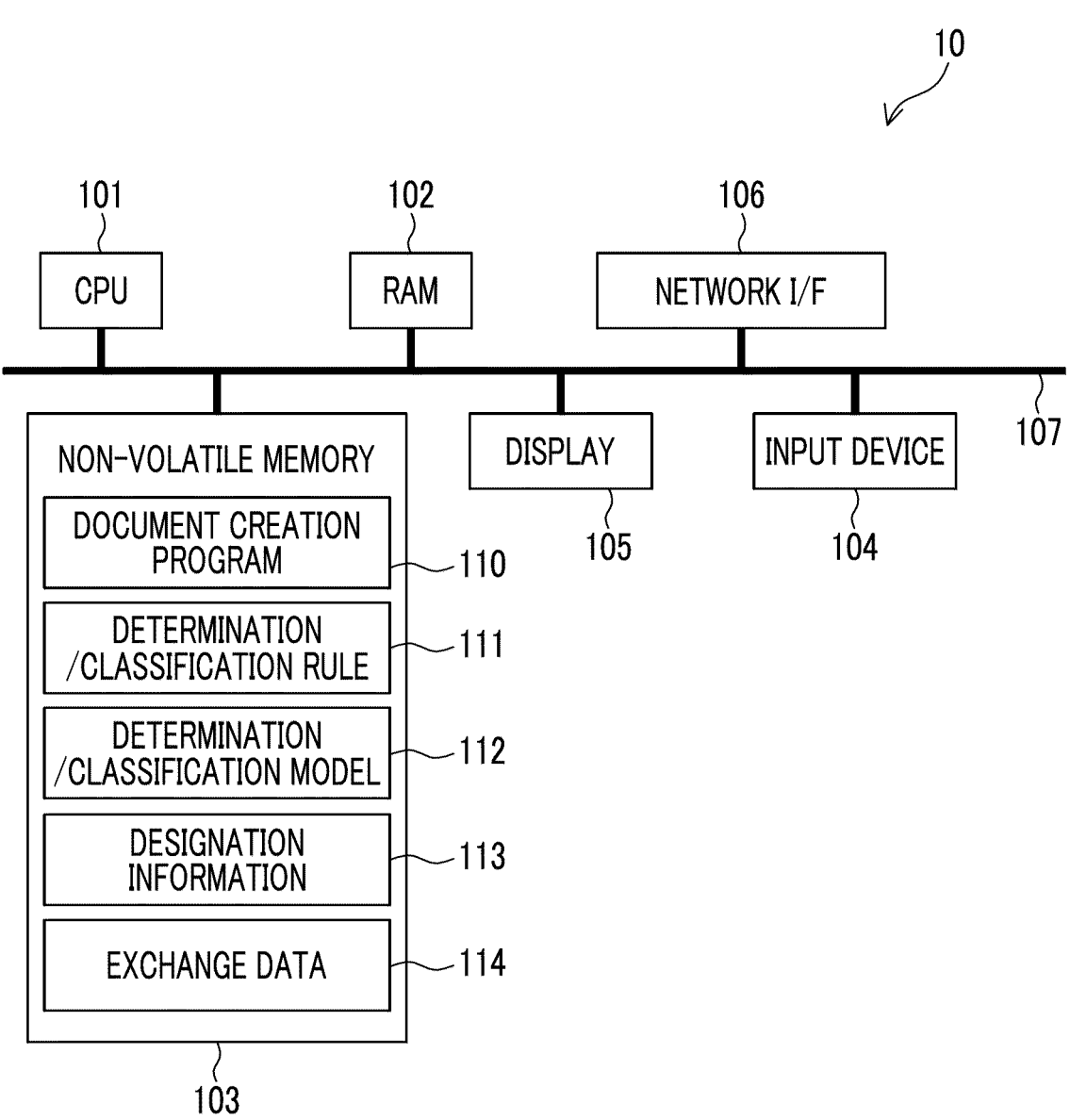
FIG. 3 is a diagram showing an example of a hardware configuration of the information processing apparatus according to the embodiment of the disclosed technology.

FIG. 3 is a diagram showing an example of a hardware configuration of the information processing apparatus 10. The information processing apparatus 10 includes a central processing unit (CPU) 101, a random access memory (RAM) 102, a non-volatile memory 103, an input device 104 including a keyboard, a mouse, and the like, a display 105, and a network interface 106. These pieces of hardware are connected to a bus 107.

For example, the display 105 is a liquid crystal display or a light emitting diode (LED) display. Further, the input device 104 may be any one of a near input device, such as a touch panel display, a voice input device, such as a microphone, or a contactless input device, such as a camera or a sensor. The network interface 106 is an interface for connecting the information processing apparatus 10 to a network. The non-volatile memory 103 is a storage medium, such as a hard disk and a flash memory. A document creation program 110, a determination/classification rule 111, a determination/classification model 112, designation information 113, and exchange data 114 are stored in the non-volatile memory 103. Those operations are described in detail later.

The RAM 102 is a work memory for the CPU 101 to execute a process. The CPU 101 loads the document creation program 110 stored in the non-volatile memory 103 to the RAM 102 and executes a process according to the document creation program 110. The CPU 101 is an example of a "processor" in the disclosed technology. The determination/classification rule 111 is an example of a "predetermined rule" in the disclosed technology. The determination/classification model 112 is an example of a "trained model" according to the disclosed technology.

Figure 4:
FIG. 4 is a diagram showing an example of a content of designation information according to the embodiment of the disclosed technology.

FIG. 4 is a diagram showing an example of a content of the designation information 113. The designation information 113 is information for designating, for each record item 35, a derivation method applied to derive the record information 31 to be recorded in the second medical document data 30 by the information processing apparatus 10. A plurality of derivation methods in which priority orders are set are designated in each record item 35. Items 1 to 4 in FIG. 4 correspond to the record items 35 included in the second medical document data 30. In the designation information 113 illustrated in FIG. 4, for example, a first derivation method is designated as a derivation method with the first priority order to be applied to derive the record information 31 to be recorded in [Item 1], and a second derivation method is designated as a derivation method with the second priority order. Further, a third derivation method is designated as a derivation method with the first priority order to be applied to derive the record information 31 to be recorded in [Item 2], and a second derivation method is designated as a derivation method with the second priority order. The designation information 113 may be predetermined or may be optionally determined by a user.

The first derivation method is a method of deriving the record information 31 by diversion from the patient information 21 included in the first medical document data 20. The second derivation method is a method of deriving the record information 31 by performing determination or classification based on the predetermined rule regarding the patient information 21 included in the first medical document data 20. The third derivation method is a method of deriving the record information 31 by performing determination or classification using a trained model regarding the patient information included in the first medical document data 20. In the designation information 113, information indicating which item of the patient information 21 need to be referred to in order to derive the record information 31 may be designated for each derivation method of each record item 35.

Figure 5:
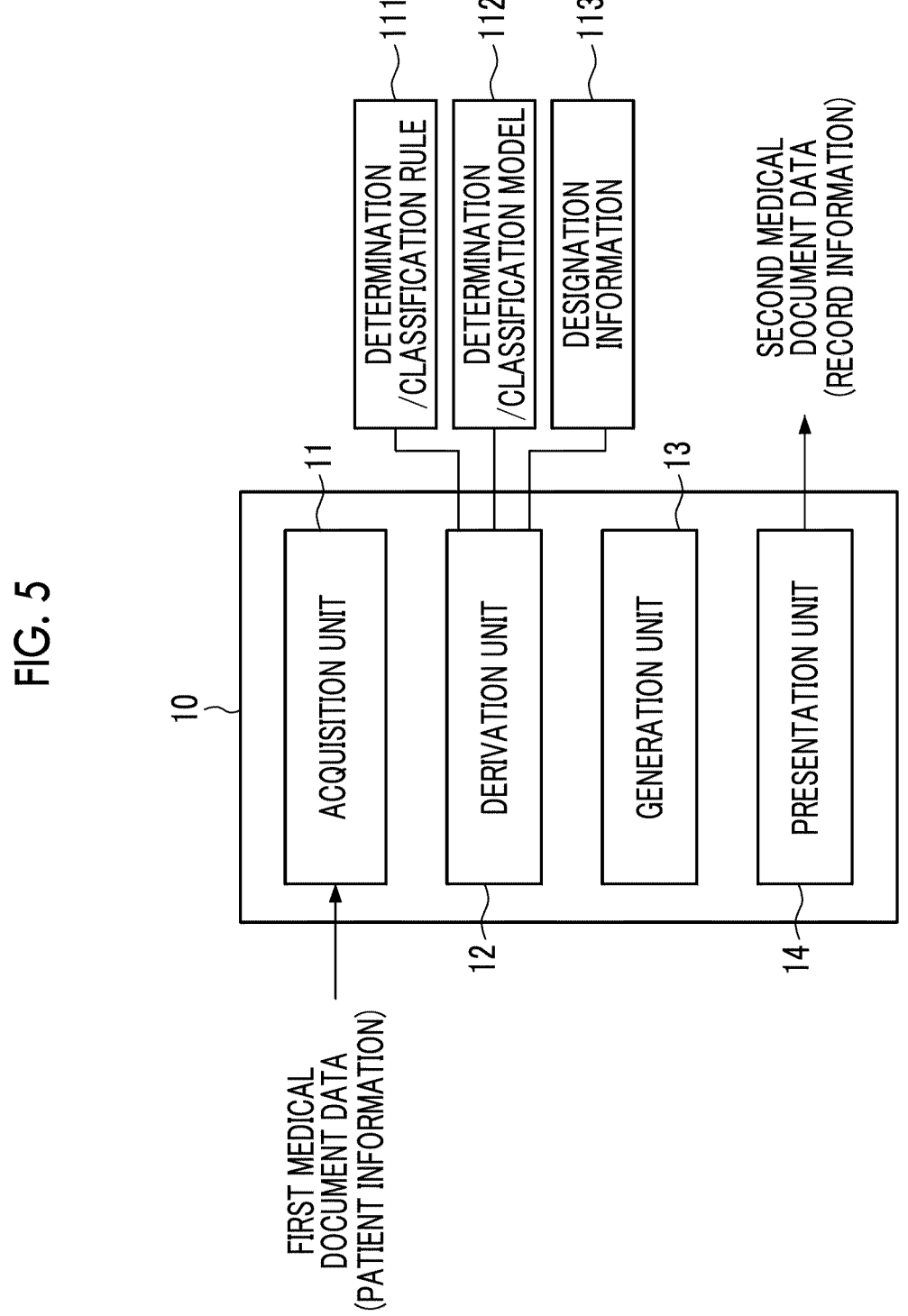
FIG. 5 is a functional block diagram showing an example of a functional configuration of the information processing apparatus according to the embodiment of the disclosed technology.

FIG. 5 is a functional block diagram showing an example of a functional configuration of the information processing apparatus 10. The information processing apparatus 10 includes an acquisition unit 11, a derivation unit 12, a generation unit 13, and a presentation unit 14. The information processing apparatus 10 functions as the acquisition unit 11, the derivation unit 12, the generation unit 13, and the presentation unit 14 by the CPU 101 executing the document creation program 110.

The acquisition unit 11 acquires the first medical document data 20 including the patient information 21. First medical document corresponding to the first medical document data 20 is created by, for example, a care manager who holds an interview with the patient, the patient's family, or these people immediately before a timing of the hospital admission, for example. The first medical document data 20 is generated by converting the first medical document into data. Further, the acquisition unit 11 acquires the designation information 113 stored in the non-volatile memory 103.

The derivation unit 12 derives the record information 31 for each of the record items 35 based on the patient information 21 included in the first medical document data 20. At this time, the derivation unit 12 derives the record information 31 by applying the derivation methods selected according to the priority order set for the record item 35 from among the plurality of derivation methods designated through the designation information 113, regarding the record item 35 corresponding to the record information 31 to be derived.

The derivation unit 12 derives the record information 31 by diversion from the patient information 21 included in the first medical document data 20 by applying the first derivation method set as the first priority order regarding [Item 1], which is one of the record items 35, according to the designation information 113 illustrated in FIG. 4. In a case where the record information 31 cannot be derived by using the first derivation method, the derivation unit 12 derives the record information 31 by performing the determination or classification based on the determination/classification rule 111 regarding the patient information 21 included in the first medical document data 20 by applying the second derivation method set as the second priority order according to the designation information 113 illustrated in FIG. 4. The determination/classification rule 111 is data for defining a rule that is applied to perform the determination or classification regarding the patient information 21.

For example, in a case where the record information 31 to be recorded in [Item 1] is the patient's "age", the derivation unit 12 derives "age" as the record information 31 to be recorded in [Item 1] by performing diversion on "age" as the patient information 21 included in the first medical document data 20 by applying the first derivation method set as the first priority order according to the designation information 113 illustrated in FIG. 4. However, for example, in a case in which "age" is not included in the first medical document data 20, "age" as the record information 31 cannot be derived by using the first derivation method. In this case, the derivation unit 12 derives "age" as the record information 31 from "date of birth" as the patient information 21 included in first medical document data 20 by using the determination/classification rule 111 by applying the second derivation method set as the second priority order according to the designation information 113 illustrated in FIG. 4. In the determination/classification rule 111, a method (formula) for deriving the age from the date of birth is defined.

The derivation unit 12 derives the record information 31 by performing the determination/classification through the determination/classification model 112 regarding the patient information 21 included in the first medical document data 20 by applying the third derivation method set as the first priority order regarding [Item 2], which is one of the record items 35, according to the designation information 113 illustrated in FIG. 4. The determination/classification model 112 is a trained model that is trained through machine learning, which uses a plurality of combinations of the patient information 21 and the record information 31 as training data, that uses the patient information 21 as an input, and that uses the record information 31 as an output. It is preferable that the determination/classification model 112 is built by using combinations of the patient information 21 and the record information 31, which are obtained for a plurality of patients, as training data. Accordingly, various cases are covered in the training data, and the accuracy of determination or classification in the determination/classification model 112 can be improved.

In a case where the record information 31 cannot be derived by using the third derivation method, the derivation unit 12 derives the record information 31 by performing the determination or classification based on the determination/classification rule 111 regarding the patient information 21 included in the first medical document data 20 by applying the second derivation method set as the second priority order according to the designation information 113 illustrated in FIG. 4.

FIG. 6 is a diagram showing an example of an aspect in which the derivation unit 12 derives the record information 31 by using the third derivation method regarding [Item 2]. In FIG. 6, a case is illustrated in which the patient information 21, which indicates the patient's recent eating status and the necessity of nursing care or assistance in activities of daily living, is input to the trained determination/classification model 112, and the determination/classification model 112 derives the record information 31, which indicates the necessity of nursing care or assistance regarding the patient's overall ADL.

The derivation unit 12 cannot derive the record information 31 by using the third derivation method in a case where omission has occurred in a part of the patient information 21 required for deriving the record information 31 regarding [Item 2]. In this case, the derivation unit 12 derives the record information 31 by applying the second derivation method according to the designation information 113 illustrated in FIG. 4.

FIG. 7 is a diagram showing an example of an aspect in which the derivation unit 12 derives the record information 31 by using the second derivation method regarding [Item 2]. In the determination/classification rule 111 illustrated in FIG. 7, in a case where three or more items of Q2 and Q3 in the first medical document data 20 are checked, a determination is made that it needs to be determined that nursing care or assistance is necessary for the overall ADL. The derivation unit 12 derives the record information 31 indicating a necessity of nursing care or assistance regarding the patient's overall ADL based on the patient information 21 in which omission has occurred a part of the patient information 21 as illustrated in FIG. 7 and the determination/classification rule 111.

The derivation unit 12 derives the record information 31 by diversion from the patient information 21 included in the first medical document data 20 by applying the first derivation method set as the first priority order regarding [Item 3] of the record items 35, according to the designation information 113 illustrated in FIG. 4. In a case where the record information 31 cannot be derived by using the first derivation method set as the first priority order due to a reason such as omission of the patient information 21, which is a diversion target, from the first medical document data 20, or the like, the derivation unit 12 derives the record information 31 by diversion from the patient information 21 included in data (for example, electronic medical records) other than the first medical document data 20 by applying the first derivation method set as the second priority order according to the designation information 113 illustrated in FIG. 4.

The derivation unit 12 derives the record information 31 by performing the determination/classification through the determination/classification model 112 regarding the patient information 21 included in the first medical document data 20 by applying the third derivation method set as the first priority order regarding [Item 4] of the record items 35, according to the designation information 113 illustrated in FIG. 4. In a case where the record information 31 cannot be derived by using the third derivation method set as the first priority order due to a reason such as omission of a part of the patient information 21 required for deriving the record information 31, the derivation unit 12 derives the record information 31 by performing the determination or classification based on another determination/classification model 112 by applying the third derivation method set as the second priority order according to the designation information 113 illustrated in FIG. 4.

Figure 8A:
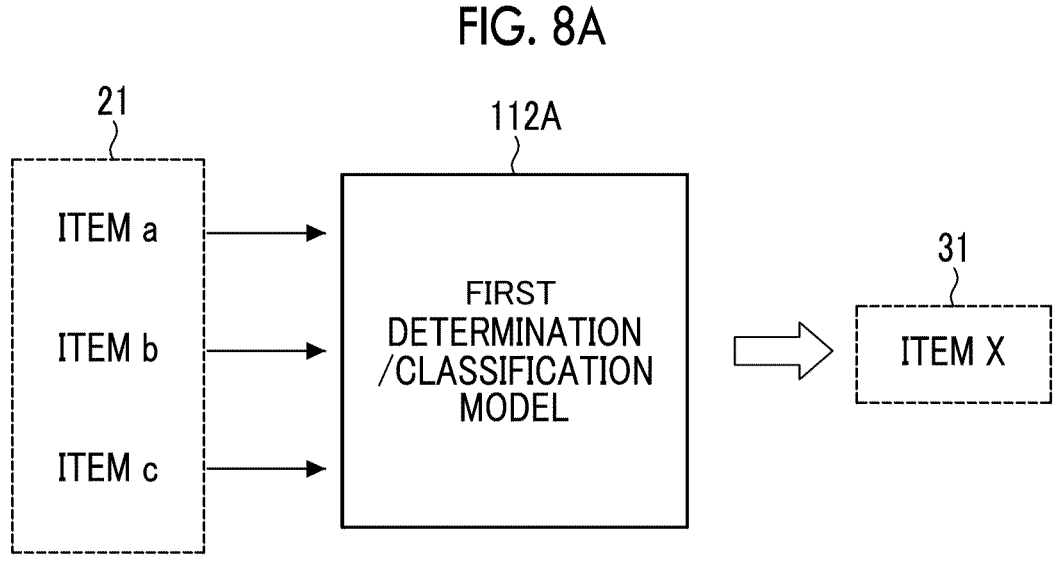
FIG. 8A is a diagram showing an input and output of a first determination/classification model according to the embodiment of the disclosed technology.
Figure 8B:
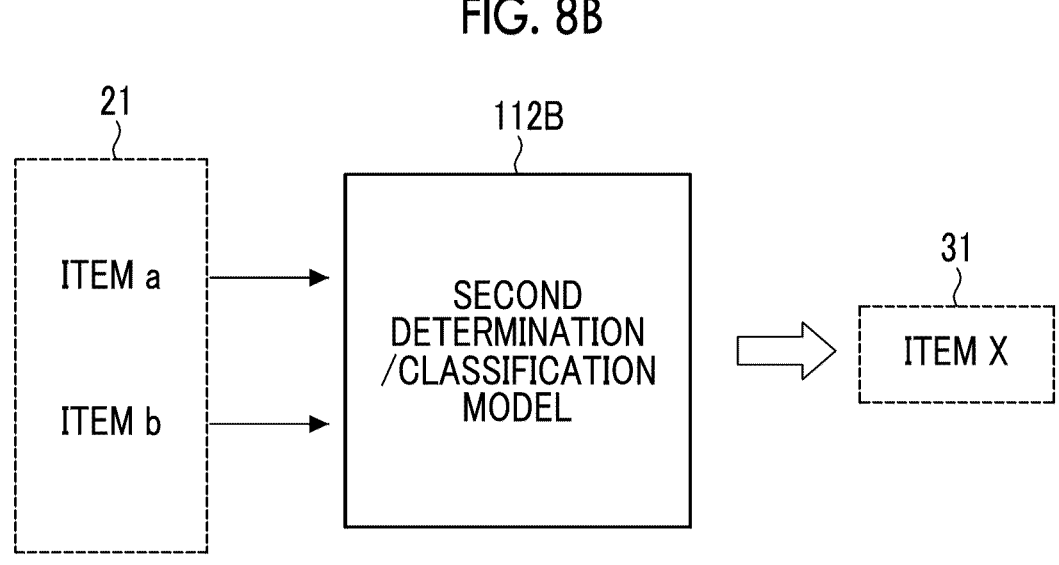
FIG. 8B is a diagram showing an input and output of a second determination/classification model according to the embodiment of the disclosed technology.

That is, determination/classification models are used according to the omitted items of the patient information 21 by creating a plurality of determination/classification models in which the number and combination of items of the patient information 21 to be input are different from each other. Specifically, a first determination/classification model 112A, in which Item a, Item b, and Item c of the patient information 21 are used as inputs and Item X of the record information 31 is used as an output as illustrated in FIG. 8A, and a second determination/classification model 112B, in which Item a and Item b of the patient information 21 are used as inputs and Item X of the record information 31 is used as an output as illustrated in FIG. 8B, are prepared in advance. In a case where the patient information 21 is applied for Item a, Item b, and Item c, the first determination/classification model 112A is used. That is, the first determination/classification model 112A is a trained model used in a case where the third derivation method set as the first priority order is applied. On the other hand, in a case where the patient information 21 is applied for Item a and Item b (that is, in a case where Item c is omitted), the second determination/classification model 112B is used. That is, the second determination/classification model 112B is a trained model used in a case where the third derivation method set as the second priority order is applied.

The generation unit 13 generates the second medical document data 30 in which the record information 31 derived by the derivation unit 12 is recorded in the corresponding record item 35. A format of the second medical document data 30 may be predetermined, and the generation unit 13 may generate the second medical document data 30 by recording the corresponding record information 31 in the record item 35 prepared in advance.

The presentation unit 14 presents the second medical document data 30 generated by the generation unit 13. The presentation of the second medical document data 30 may be performed, for example, by displaying the second medical document data 30 on the display 105 or may be performed by outputting a second medical document corresponding to the second medical document data 30 from a printer (not shown) in response to a request of the user.

Figure 9:
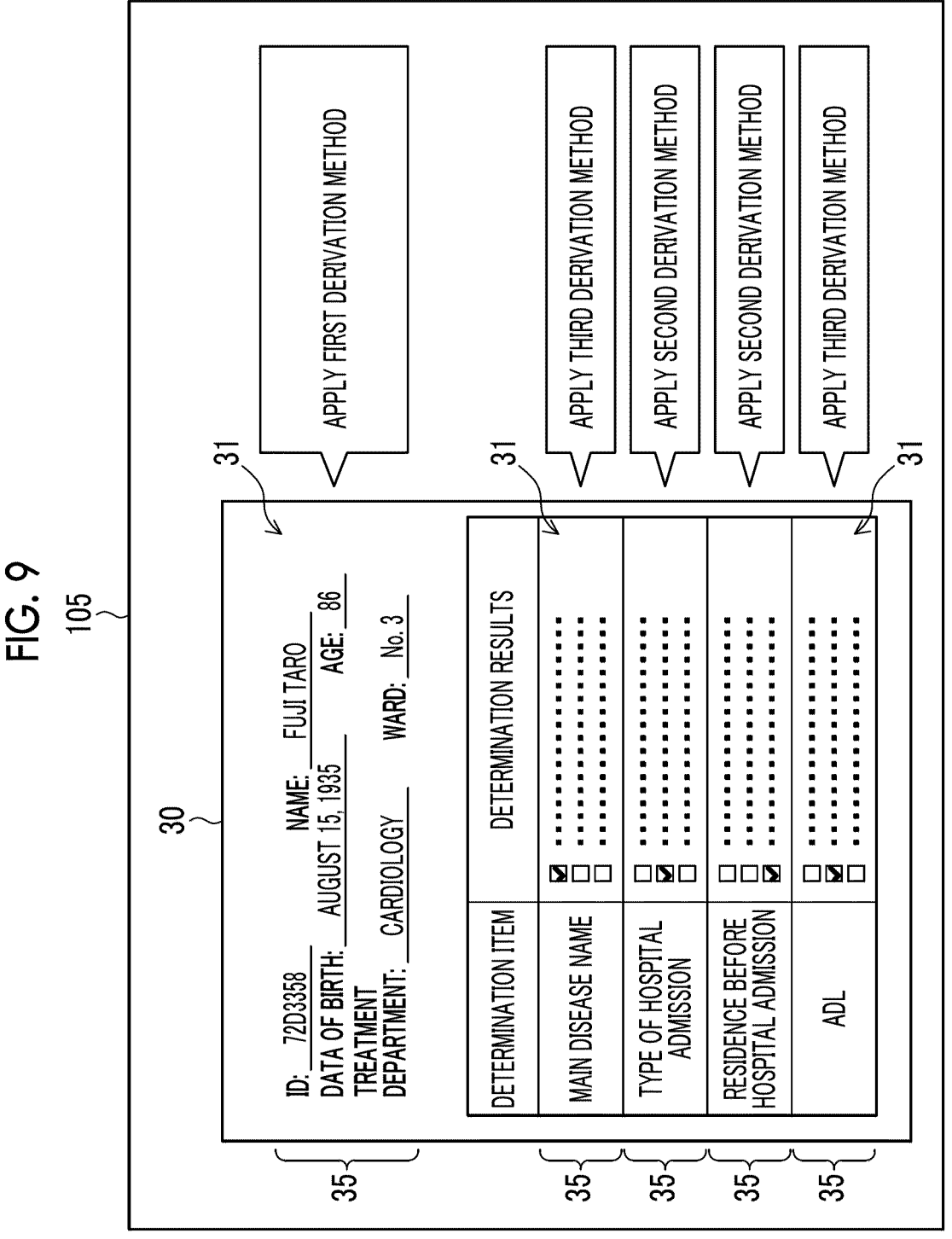
FIG. 9 is a diagram showing an example of a display form of the second medical document data displayed on a display.

FIG. 9 is a diagram showing an example of a display form of the second medical document data 30 displayed on the display 105. As illustrated in FIG. 9, the presentation unit 14 presents the second medical document data 30 by associating information, which indicates a derivation method applied to derive the record information 31 among the first to third derivation methods, with the record information 31. Accordingly, for each piece of record information 31 derived by the derivation unit 12, it is possible to understand whether the derivation method applied to derive the record information 31 is one of the first to third derivation methods. The display form of the information indicating the applied derivation method is not limited to the form illustrated in FIG. 9. For example, the color of at least one of the characters or the background of the record information 31 may be made different according to the applied derivation method, or an icon in accordance with the applied derivation method may be applied to the corresponding record information 31.

Figure 10:
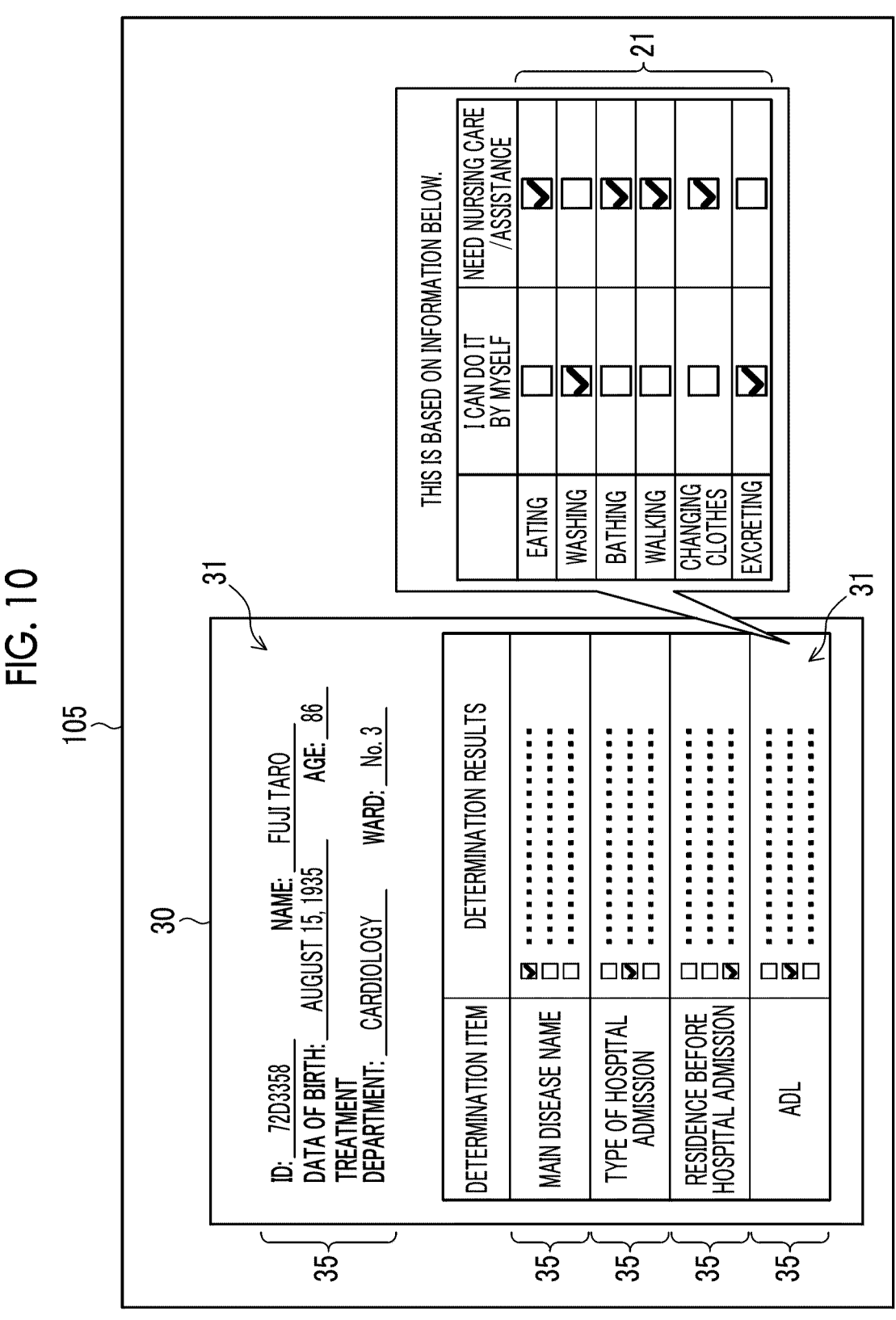
FIG. 10 is a diagram showing an example of a display form of the second medical document data displayed on the display.

FIG. 10 is a diagram showing another example of a display form of the second medical document data 30 displayed on the display 105. As illustrated in FIG. 10, the presentation unit 14 may present the second medical document data 30 by associating the patient information 21, which is used for deriving the record information 31, with the corresponding record information 31. In the example shown in FIG. 10, regarding the record item 35 related to ADL in which the record information 31 is recorded, the patient information 21 that is the basis for deriving the record information 31 is displayed on the right side of the record item 35 related to the ADL. By performing such basis display, work of checking the appropriateness for the record information 31 derived by the derivation unit 12, is facilitated. A format of a field where the patient information 21 is presented is not limited thereto. A display position of the patient information 21 is not limited thereto as long as a correspondence relationship with the record information 31, which is derived based on the patient information 21, is clear. For example, in a case where Item 1 is the record information 31, the patient information 21, which is used as a basis for deriving the record information 31, may be displayed between Item 1 and Item 2. Further, the patient information 21, which is used as a basis for deriving the record information 31, may be always displayed in a case of presenting the second medical document data 30, and in a case where the record information 31 is designated, the patient information 21, which is a basis for deriving the record information 31, may be displayed as a pop-up. The designation of the record information 31 may be performed by, for example, receiving an input from the user with respect to a display field of an item, an automatic input icon, or the like by the input device 104.

By the way, in the first medical document data 20, the item name of the patient information 21 may be different for each medical institution. Similarly, in the second medical document data 30, the item name of the record item 35 may be different for each medical institution. In this way, in a case where the item names used in the first medical document data 20 and the second medical document data 30 are inconsistent, a situation may occur where item names at the time of training of input and output information of the determination/classification model 112 and item names used in the first medical document data 20 and second medical document data 30 do not coincide with each other.

Figures 11A, 11B:
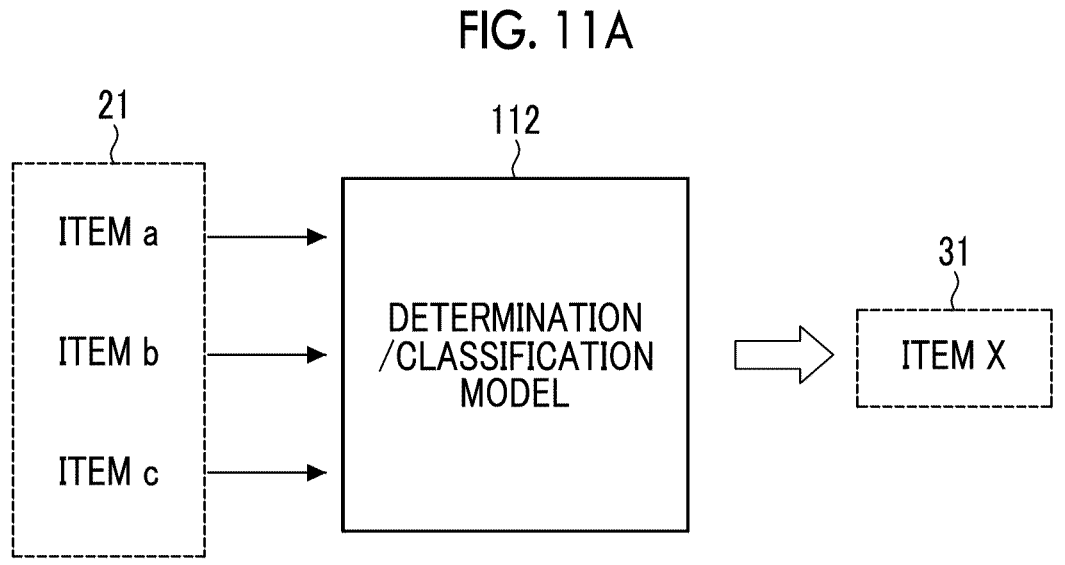
FIG. 11A is a diagram showing an input and output of a determination/classification model according to the embodiment of the disclosed technology.
FIG. 11B is a diagram showing an example of a content of exchange data according to the embodiment of the disclosed technology.

FIG. 11A shows the determination/classification model 112 in which the patient information 21, where item names at the time of training are defined as a, b, and c, is used as an input and the record information 31, where an item name at the time of training is defined as x, is used as an output. In a case where the item names used in the first medical document data 20 are inconsistent, in the first medical document data 20, a situation may occur in which the patient information 21 where item names coincide with a, b, and c is not present. In this case, even though the patient information 21 to be input to the determination/classification model 112 is included in the first medical document data 20, it becomes difficult to extract desired patient information 21 from the first medical document data 20 due to the inconsistent item name. For example, the above problem may occur in a case where the item name of the patient information 21 at the time of training of the determination/classification model 112 is a "main disease name" and the item name of the patient information 21 actually used in the first medical document data 20 is a "main illness name".

Similarly, in a case where the item names of the record items 35 used in the second medical document data 30 are inconsistent, in the second medical document data 30, a situation may occur in which the record item 35 where the item name coincides with x is not present. In this case, even though the record item 35, in which the record information 31 output from the determination/classification model 112 is to be recorded, is included in the second medical document data 30, it becomes difficult to specify the desired record item 35 due to the inconsistent item name. For example, the above problem may occur in a case where the item name of the record item 35 at the time of training of the determination/classification model 112 is "whether it is malignant tumor or not" and the item name of the record item 35 actually used in the second medical document data 30 is "whether it is cancer or not".

Therefore, the information processing apparatus 10 comprises exchange data 114 for absorbing the difference between the item names at the time of training of input and output information of the determination/classification model 112 and the item names actually used in the first medical document data 20 and the second medical document data 30. FIG. 11B is a diagram showing an example of a content of the exchange data 114. The exchange data 114 is data indicating a correspondence relationship between the item names (expressed as actually-used item-name in FIG. 11B) actually used in the first medical document data 20 or the second medical document data 30 and the item names (expressed as time-of-training item name in FIG. 11B) at the time of training of the determination/classification model, for each of the patient information 21 and the record information 31.

In a case where the third derivation method is applied, the derivation unit 12 specifies the patient information 21, which has actually used item names (D, E, F) corresponding to the item names (a, b, c) at the time of training of the patient information 21, from the first medical document data 20, by using the exchange data 114. The derivation unit 12 derives the record information 31 by inputting the specified patient information 21 to the determination/classification model 112.

The generation unit 13 specifies the record item of an item name (Y) corresponding to an item name (x) at the time of training, by using the exchange data 114. The generation unit 13 generates the second medical document data 30 in which the record information 31, which is output from the determination/classification model 112, is recorded in the specified record item 35.

Figure 12:
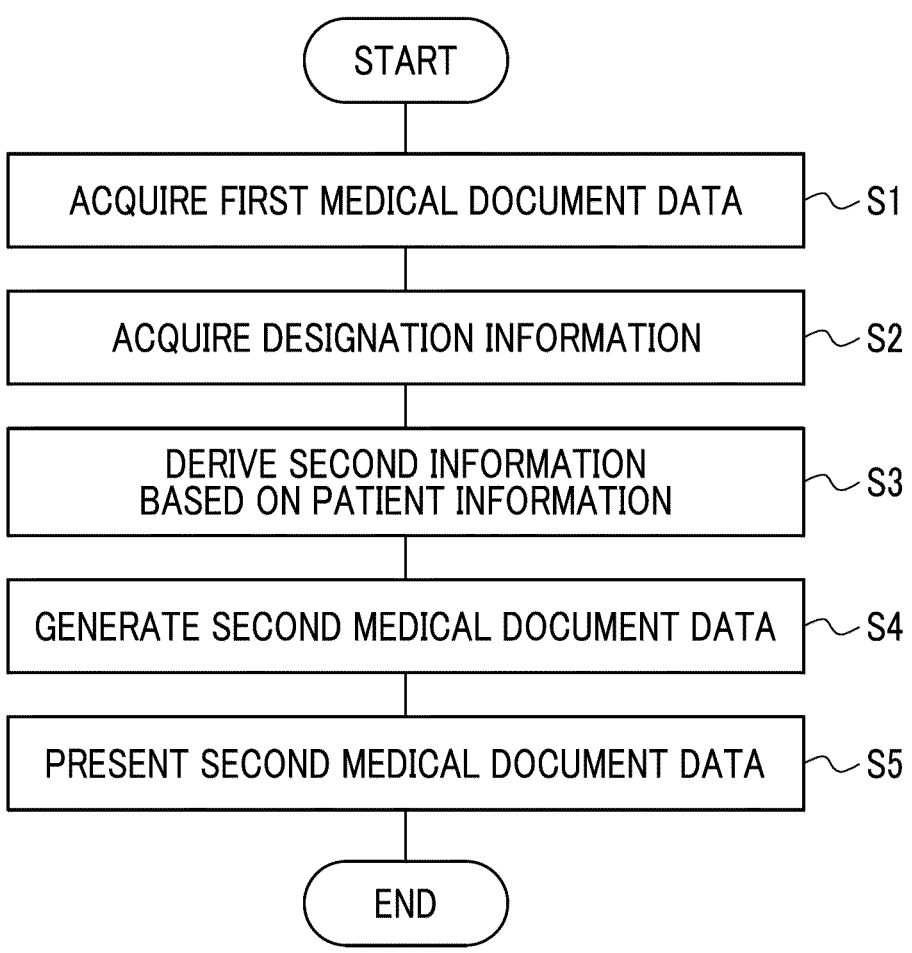
FIG. 12 is a flowchart showing an example of a flow of a process that is performed by executing a document creation program according to the embodiment of the disclosed technology.

FIG. 12 is a flowchart showing an example of a flow of a process that is performed by executing the document creation program 110 by the CPU 101. The document creation program 110 is executed, for example, in a case where the user issues an instruction to start the process by operating the input device 104.

In step S1, the CPU 101 functions as the acquisition unit 11 and acquires the first medical document data 20 including the patient information 21 related to the patient. In step S2, the CPU 101 functions as the acquisition unit 11 and acquires the designation information 113 stored in the non-volatile memory 103. In a case where the user defines the content of the designation information 113, the user performs a designation input to designate the plurality of derivation methods where the priority orders are applied for each record item, by using the input device 104. The CPU 101 receives the designation input, which is made by the user, and stores designation information 113 corresponding to the designation input in the non-volatile memory 103.

In step S3, the CPU 101 functions as the derivation unit 12 and derives the record information 31 based on the patient information 21 included in the first medical document data 20 acquired in step S1. At this time, the CPU 101 derives the record information 31 by applying the derivation methods selected according to the priority order set for the record item 35 from among the plurality of derivation methods designated through the designation information 113, regarding the record item 35 corresponding to the record information 31 to be derived. The CPU 101 derives the record information 31 by using the derivation method where a relatively low priority order is set in a case where the record information 31 cannot be derived by using the derivation method where a relatively high priority order is set among the derivation methods designated for each record item 35 in the designation information 113.

The CPU 101 derives the record information 31 by diversion from the patient information 21, regarding the record item 35 to which the first derivation method is applied. The CPU 101 derives the record information 31 based on the determination/classification rule 111, regarding the record item 35 to which the second derivation method is applied. Further, the CPU 101 derives the record information 31 by using the determination/classification model 112, regarding the record item 35 to which the third derivation method is applied.

In step S4, the CPU 101 functions as the generation unit 13 and generates the second medical document data 30 in which the record information 31, which is derived in step S3, is recorded in the corresponding record item 35.

In step S5, the CPU 101 functions as the presentation unit 14 and presents the second medical document data 30, which is generated in step S4, for example, by displaying the second medical document data 30 on the display 105.

As described above, the information processing apparatus 10 according to the present embodiment acquires designation information 113 for designating the plurality of derivation methods to derive the record information 31 to be recorded in at least one record item 35 related to the patient, derives the record information 31 by applying the derivation method, which is selected according to a preset priority order from among the plurality of derivation methods designated through the designation information 113, based on the patient information 21 related to the patient, for the record item 35, and generates the medical document data in which the derived record information 31 is recorded in the record item 35.

The hospital discharge support risk screening sheet includes an item for transferring the patient information entered in the previously created information sheet at the time of hospital admission and an item for entering the result obtained by performing the determination or classification based on the patient information entered in the information sheet at the time of hospital admission. Therefore, the medical worker who creates the hospital discharge support risk screening sheet is pressured to check the patient information entered in the information sheet at the time of hospital admission. Further, at present, since the standards for performing such determinations or classifications based on the patient information are not clear, situations have arisen in which different determinations or classifications are made depending on the work history or knowledge of the medical worker.

According to the information processing apparatus 10 of the present embodiment, it is possible to reduce the burden of the checking work of the patient information in a case where the medical document corresponding to the second medical document data 30 is created. Further, regarding the information recorded in the medical documents, it is possible to avoid a situation where different determinations or classifications are made depending on the work history or knowledge of the medical worker. That is, according to the information processing apparatus 10 of the present embodiment, as compared with a case where the plurality of derivation methods are not designated as derivation methods for deriving the record information 31 to be recorded in at least one record item 35 related to the patient, it is possible to effectively support the creation of the medical documents.

Further, the medical document, which is created from before the hospital admission of the patient to after the hospital discharge, is created by different people at a plurality of time points. The patient information 21 includes an item for performing a text input, an item that requires examination, or an item that requires determination of the medical worker, and omission may occur in the patient information 21 depending on the user, who performs an input or the patient's medical condition. Further, in a case where information that needs to be managed as the patient information 21 is revised due to legal regulations such as the medical act or the like, omission may occur in the patient information 21 according to the creation time point. According to the information processing apparatus 10 of the present embodiment, since the plurality of derivation methods for deriving the record information 31 to be recorded in at least one record item 35 related to the patient are designated, it is possible to effectively support the creation of the medical documents in a case where omission has occurred in the patient information 21, as compared with a case where a single derivation method is designated.

Further, according to the information processing apparatus 10 of the present embodiment, even in a case where the record information 31 cannot be derived by using the derivation method where a relatively high priority order is set among the plurality of derivation methods, the record information 31 is derived by using the derivation method where a relatively low priority order is set, thereby, for example, even in a case where omission has occurred in a part of the patient information 21, the record information 31 can be derived.

In the above description, although a case has been exemplified in which the first medical document data 20 corresponds to the information sheet at the time of hospital admission (or the information coordination sheet at the time of hospital admission), and the second medical document data 30 corresponds to the hospital discharge support risk screening sheet, the disclosed technology is not limited to this aspect. The first medical document data 20 may correspond to the hospital discharge support risk screening sheet, and the second medical document data 30 may correspond to a hospital discharge support plan document. The purpose of the hospital discharge support plan document is to support the patient being discharged from the hospital with peace of mind and satisfaction and to support the patient such that he or she can continue to receive medical treatment and maintain a lifestyle in a familiar area at an early stage.

In a case where the second medical document data 30 corresponds to the hospital discharge support plan document, examples of the record information 31 recorded in the second medical document data 30 include information indicating the necessity of continuation of rehabilitation. In this case, examples of the plurality of pieces of patient information 21 used for deriving the record information 31 include information indicating a patient's age, the purpose of hospital admission, a nursing care insurance certification standard, a necessity of assistance in walking, a necessity of assistance in bathing, whether a patient lives alone or not, whether a patient was using a wheelchair at the stage of hospital admission, and whether a patient was using a cane at the stage of hospital admission.

Further, another example of the record information 31 in a case where the second medical document data 30 corresponds to the hospital discharge support plan document includes information indicating whether an expected hospital discharge destination is home. In this case, examples of the plurality of pieces of patient information 21 used for deriving the record information 31 include information indicating a patient's age, the purpose of hospital admission, a nursing care insurance certification standard, whether a patient has forgetfulness that interferes with daily life, and whether medical devices (colostomy, blood sugar-related device, oxygen-related device) are used. The patient information 21 exemplified above is information that is acquired from the information sheet at the time of hospital admission or the hospital discharge support risk screening sheet created at a time point before the creation time point of the hospital discharge support plan document. Further, the disclosed technology can also be applied to a case of creating medical documents other than the document related to the hospital admission and discharge of the patient.

Further, an information source in which the patient information 21 is recorded is not limited to the document data, and any information source may be used. For example, the patient information 21 may be information recorded in an electronic medical record or may be information recorded in a database created for the patient. Further, the patient information 21 may be included in a plurality of pieces of medical document data. For example, the medical document corresponding to the hospital discharge support plan document may be output as the second medical document data 30 by using two medical documents, which are a medical document corresponding to the information sheet at the time of hospital admission and a medical document corresponding to the risk screening sheet, as the first medical document data. Based on the patient information 21 acquired from the medical documents created at such a plurality of different time points, in a case where the medical document data is generated by deriving the record information 31, or in a case where information that needs to be managed as the patient information 21 is revised due to legal regulations such as the medical act or the like, the possibility in which omission occurs in the patient information 21 increases according to the creation time point. Even in such cases, according to the information processing apparatus 10 of the present embodiment, since the record information 31 is derived by applying the derivation method selected according to the preset priority order from among the plurality of derivation methods for deriving the record information 31 to be recorded in at least one record item 35 related to the patient, it is possible to effectively support the creation of the medical documents as compared with a case where a single derivation method is designated.

Further, in the above description, although a case where the entire record information 31 is derived by the derivation unit 12 has been exemplified, a part of the record information 31 may be provided through a manual input of the user. In this case, the presentation unit 14 may display the second medical document data 30 on the display 105 such that the record information 31, which is derived by the derivation unit 12, and the record information 31, which is recorded through a manual input, are in an identifiable state from each other.

Further, in the above embodiment, for example, as hardware structures of processing units that execute various processes, such as the acquisition unit 11, the derivation unit 12, the generation unit 13, and the presentation unit 14, various processors shown below can be used. The above-described various processors include, for example, a programmable logic device (PLD) which is a processor having a changeable circuit configuration after manufacturing, such as an FPGA, and a dedicated electrical circuit which is a processor having a dedicated circuit configuration designed to execute specific processing, such as an application specific integrated circuit (ASIC), in addition to the GPU and the CPU which is a general-purpose processor that executes software (programs) to function as various processing units, as described above.

One processing unit may be configured by one of the various processors or may be configured by a combination of the same or different kinds of two or more processors (for example, a combination of a plurality of FPGAs or a combination of the CPU and the FPGA). Further, a plurality of processing units may be configured by one processor.

As an example in which a plurality of processing units are configured by one processor, first, there is a form in which one processor is configured by a combination of one or more CPUs and software as typified by a computer, such as a client or a server, and this processor functions as a plurality of processing units. A second example thereof is a form of using a processor that realizes the function of the entire system including the plurality of processing units by one integrated circuit (IC) chip, as represented by a system on chip (SoC) or the like. In this way, various processing units are configured by one or more of the above-described various processors as hardware structures.

Furthermore, as the hardware structure of the various processors, more specifically, an electrical circuit (circuitry) in which circuit elements such as semiconductor elements are combined can be used.

Moreover, in the above-described embodiment, an aspect has been described in which the document creation program 110 is stored (installed) in advance in the non-volatile memory 103, but the disclosed technology is not limited to this. The document creation program 110 may be provided in a form recorded in a recording medium such as a compact disc read only memory (CD-ROM), a digital versatile disc read only memory (DVD-ROM), and a universal serial bus (USB) memory. In addition, the document creation program 110 may be configured to be downloaded from an external device via a network. That is, the program (program product) described in the present embodiment may be provided by a recording medium or may be distributed from an external computer.

Further, the disclosure of JP2021-169822 filed on Oct. 15, 2021 is incorporated herein by reference in its entirety. Further, all documents, patent applications, and technical standards described in the specification are incorporated herein by references to the same extent as the incorporation of the individual documents, patent applications, and technical standards by references are described specifically and individually.

What is claimed is:

1. An information processing apparatus comprising:
a memory, storing designation information which designates, for each record item, a plurality of trained models set as a plurality of derivation methods and a preset priority order corresponding to each of the plurality of derivation methods, and exchange data which indicates a correspondence relationship between an item name actually used in a first medical document data and an item name used at a time of training of the plurality of trained models; and
at least one processor,
wherein the processor is configured to:
acquire the first medical document data including patient information related to a patient,
acquire the designation information stored in the memory to derive record information to be recorded in the record item related to the patient;
specify, by using the exchange data, the patient information of the item name actually used in the first medical document data that corresponds to the item name used at the time of training for a first trained model; wherein the patient information for the first trained model includes a first combination of items;
derive the record information for the record item by inputting the first combination of items into the first trained model set as a first derivation method, which is selected according to the preset priority order from among the plurality of derivation methods designated through the designation information;
in a case where at least one item in the first combination is omitted and the record information is not capable of being derived by using the first trained model:
specify, by using the exchange data, the patient information of the item name actually used in the first medical document data that corresponds to the item name used at the time of training for a second trained model, wherein the second trained model is set as a second derivation method having a lower priority in the preset priority order with respect to the first derivation method, and the patient information for the second trained model includes a second combination of items;
derive the record information for the record item by inputting the second combination of items into the second trained model,
wherein the plurality of trained models are trained in advance for performing determination or classification according to missing information of the patient information by using a plurality of combinations of the patient information and the record information, which are obtained for a plurality of patients, as training data, wherein a number and combination of items of the patient information to be input are different from each other among the plurality of the trained models;

generate second medical document data in which the derived record information is recorded in the record item; and output a second medical document corresponding to the second medical document data from a printer in response to a request of a user.

2. The information processing apparatus according to claim 1, wherein the plurality of derivation methods for deriving the record information further comprise: diversion from the patient information, and performing determination or classification based on a predetermined rule regarding the patient information.

3. The information processing apparatus according to claim 1, wherein the processor is configured to present the medical document data by associating information, which indicates the derivation method applied to derive the record information from among the plurality of derivation methods, with the record information.

4. The information processing apparatus according to claim 1, wherein the processor is configured to present the medical document data by associating the patient information, which is used to derive the record information, with the record information.

5. The information processing apparatus according to claim 1, wherein the processor is configured to receive a designation input of the designation information.

6. The information processing apparatus according to claim 1, wherein the medical document data is data obtained by converting documents, which are related to hospital admission and discharge of the patient, into data.

7. An information processing method executed by at least one processor included in an information processing apparatus, the method comprising:

storing designation information which designates, for each record item, a plurality of trained models set as a plurality of derivation methods and a preset priority order corresponding to each of the plurality of derivation methods in a memory; and exchange data which indicates a correspondence relationship between an item name actually used in a first medical document data and an item name used at a time of training of the plurality of trained models;

acquiring the first medical document data including patient information related to a patient;

acquiring the designation information stored in the memory to derive record information to be recorded in the record item related to the patient;

specifying, by using the exchange data, the patient information of the item name actually used in the first medical document data that corresponds to the item name used at the time of training for a first trained model; wherein the patient information for the first trained model includes a first combination of items;

deriving the record information for the record item by inputting the first combination of items into the first trained model set as a first derivation method, which is selected according to the preset priority order from among the plurality of derivation methods designated through the designation information;

in a case where at least one item in the first combination is omitted and the record information is not capable of being derived by using the first trained model:

specifying, by using the exchange data, the patient information of the item name actually used in the first medical document data that corresponds to the item name used at the time of training for a second trained model, wherein the second trained model is set as a second derivation method having a lower priority in the preset priority order with respect to the first derivation method, and the patient information for the second trained model includes a second combination of items;

deriving the record information for the record item by inputting the second combination of items into the second trained model, wherein the plurality of trained models are trained in advance for performing determination or classification according to missing information of the patient information by using a plurality of combinations of the patient information and the record information, which are obtained for a plurality of patients, as training data, wherein a number and combination of items of the patient information to be input are different from each other among the plurality of the trained models;

generating second medical document data in which the derived record information is recorded in the record item; and outputting a second medical document corresponding to the second medical document data from a printer in response to a request of a user.

8. A non-transitory computer-readable storage medium storing an information processing program causing at least one processor included in an information processing apparatus to execute a process comprising:

storing designation information which designates, for each record item, a plurality of trained models set as a plurality of derivation methods and a preset priority order corresponding to each of the plurality of derivation methods in a memory; and exchange data which indicates a correspondence relationship between an item name actually used in a first medical document data and an item name used at a time of training of the plurality of trained models;

acquiring the first medical document data including patient information related to a patient;

acquiring the designation information stored in the memory to derive record information to be recorded in the record item related to the patient;

specifying, by using the exchange data, the patient information of the item name actually used in the first medical document data that corresponds to the item name used at the time of training for a first trained model; wherein the patient information for the first trained model includes a first combination of items;

deriving the record information for the record item by inputting the first combination of items into the first trained model set as a first derivation method, which is selected according to the preset priority order from among the plurality of derivation methods designated through the designation information;

in a case where at least one item in the first combination is omitted and the record information is not capable of being derived by using the first trained model:

specifying, by using the exchange data, the patient information of the item name actually used in the first medical document data that corresponds to the item name used at the time of training for a second trained model, wherein the second trained model is set as a second derivation method having a lower priority in the preset priority order with respect to the first derivation method, and the patient information for the second trained model includes a second combination of items;

deriving the record information for the record item by inputting the second combination of items into the second trained model, wherein the plurality of trained models are trained in advance for performing determination or classification according to missing information of the patient information by using a plurality of combinations of the patient information and the record information, which are obtained for a plurality of patients, as training data, wherein a number and combination of items of the patient information to be input are different from each other among the plurality of the trained models;

generating second medical document data in which the derived record information is recorded in the record item; and outputting a second medical document corresponding to the second medical document data from a printer in response to a request of a user.

\* \* \* \* \*